(12) United States Patent
Nelson

(10) Patent No.: US 6,519,355 B2
(45) Date of Patent: Feb. 11, 2003

(54) OPTICAL PROJECTION IMAGING SYSTEM AND METHOD FOR AUTOMATICALLY DETECTING CELLS HAVING NUCLEAR AND CYTOPLASMIC DENSITOMETRIC FEATURES ASSOCIATED WITH DISEASE

(76) Inventor: Alan C. Nelson, 1509 56th Ave. Ct. NW., Gig Harbor, WA (US) 98335

( * ) Notice: Subject to any disclaimer, the term of this patent is extended or adjusted under 35 U.S.C. 154(b) by 0 days.

(21) Appl. No.: 10/055,066

(22) Filed: Jan. 22, 2002

(65) Prior Publication Data

US 2002/0150285 A1 Oct. 17, 2002

Related U.S. Application Data

(63) Continuation-in-part of application No. 09/927,151, filed on Aug. 10, 2001.
(60) Provisional application No. 60/279,244, filed on Mar. 28, 2001.

(51) Int. Cl.[7] ................................................. G06K 9/00
(52) U.S. Cl. ........................................................ 382/133
(58) Field of Search ................................. 382/133, 134; 73/53.01, 61.48; 702/19, 21, 23, 26, 32, 137, 191; 250/461.2; 430/332, 333

(56) References Cited

U.S. PATENT DOCUMENTS

| | | | | |
|---|---|---|---|---|
| 3,470,373 A | | 9/1969 | Brewer | 250/461.2 |
| 3,497,690 A | | 2/1970 | Wheeless, Jr. | 250/461.2 |
| 3,657,537 A | | 4/1972 | Wheeless, Jr. | 250/461.2 |
| 3,833,762 A | | 9/1974 | Gudmundsen | 348/208.99 |
| 3,960,449 A | | 6/1976 | Carlton | 356/340 |
| 3,999,047 A | * | 12/1976 | Green | 382/134 |
| 4,175,860 A | * | 11/1979 | Bacus | 356/39 |
| 4,293,221 A | | 10/1981 | Kay | 356/318 |
| 5,281,517 A | * | 1/1994 | Bacus et al. | 435/6 |
| 5,308,990 A | | 5/1994 | Takahashi et al. | 250/459.1 |
| 5,402,460 A | | 3/1995 | Johnson | 378/10 |
| 5,848,123 A | | 12/1998 | Strommer | 310/261 |
| 5,987,158 A | * | 11/1999 | Meyer et al. | 382/133 |
| 6,026,174 A | | 2/2000 | Palcic | 382/133 |
| 6,165,734 A | * | 12/2000 | Garini et al. | 435/7.21 |
| 6,201,628 B1 | | 3/2001 | Basiji | 359/217 |
| 6,211,955 B1 | | 4/2001 | Basiji | 356/326 |
| 6,249,341 B1 | | 6/2001 | Basiji | 356/73 |
| 6,251,586 B1 | * | 6/2001 | Mulshine et al. | 435/6 |
| 6,251,615 B1 | | 6/2001 | Oberhardt | 435/7.21 |
| 6,252,979 B1 | | 6/2001 | Lee | 382/133 |

OTHER PUBLICATIONS

Shapiro, HM, *Practical Flow Cytometry*, 3rd ed., Wiley–Liss, 1995.

Gilbert, P, "Iterative Methods for the Three dimensional Reconstruction of an Object from Projections," Journal of Theoretical Biology 36:105–17, 1972.

(List continued on next page.)

*Primary Examiner*—Andrew W. Johns
*Assistant Examiner*—Shervin Nakhjavan
(74) *Attorney, Agent, or Firm*—George A. Leone

(57) ABSTRACT

A system and method for rapidly detecting cells of interest using multi-dimensional, highly quantitative, nuclear and cytoplasmic densitometric features (NDFs and CDFs) includes a flow optical tomography (FOT) instrument capable of generating various optical projection images (or shadowgrams) containing accurate density information from a cell, a computer and software to analyze and reconstruct the projection images into a multi-dimensional data set, and automated feature collection and object classifiers. The system and method are particularly useful in the early detection of cancers such as lung cancer using a bronchial specimen from sputum or cheek scrapings and cervical/ovarian cancer using a cervical scraping, and the system can be used to detect rare cells in specimens including blood.

34 Claims, 9 Drawing Sheets

OTHER PUBLICATIONS

Oppenheim, BE, "More Accurate Algorithms for Iterative 3 dimensional Reconstruction," IEEE Transactions on Nuclear Science NS–21:72–7, 1974.

Singer, JR, Grunbaum, FA, Kohn, P, and Zubelli, JP, "Image Reconstruction of the Interior of Bodies that Diffuse Radiation," Science 248(4958):990–3, 1990.

Mueller, K and Yage, R, "Rapid 3–D Cone–beam Reconstruction with the Simultaneous Algebraic Reconstruction Technique (SART) Using 2–D Texture Mapping Hardware", IEEE Transactions on Medical imaging 19(12):1227–37, 2001.

Bellman, SH, Bender, R, Gordon, R, and Rowe, JE, "ART is Science being A Defense of Algebraic Reconstruction Techniques for Three dimensional Electron Microscopy," Journal of Theoretical Biology 32:205–16, 1971.

Manglos, SH, Jaszcak, RJ, and Floyd, CE, "Maximum Likelihood Reconstruction for Cone Beam SPECT: Development and Initial Tests," Physics in Medicine and Biology 34(12):1947–57, 1989, #1382.

Manglos, SH, Gagne, GM, Krol A, Thomas, FD, and Narayanaswamy, R, "Transmission Maximum–likelihood Reconstruction with Ordered Subsets for Cone Beam CT", Physics in Medicine and Biology 40(7):1225–41, 1995, #4389.

Hampel, U and Freyer, R, "Fast Image Reconstruction for Optical Absorption Tomography in Media with Radially Symmetric Boundaries", Medical Physics 25 (1):92–101, 1998.

Jiang, H, Paulsen, KD, and Osterberg, UL, "Frequency–domain Near–infrared Photo Diffusion Imaging: Initial Evaluation in Multitarget Tissuelike Phantoms", Medical Physics 25(2):183–93, 1998.

Herman, G, *Image Reconstruction from Projections: The Fundamentals of Computerized Tomography*, Academic Press, New York, 1980.

Paulsen, KD and Jiang, H, "Spatially Varying Optical Property Reconstruction Using a Finite Element Diffusion Equation Approximation", Medical Physics 22(691–701) 1995.

* cited by examiner

OPTICAL PROJECTION IMAGING SYSTEM AND METHOD FOR AUTOMATICALLY DETECTING CELLS HAVING NUCLEAR AND CYTOPLASMIC DENSITOMETRIC FEATURES ASSOCIATED WITH DISEASE

RELATED APPLICATIONS

This application is a continuation-in-part of co-pending U.S. application Ser. No. 09/927,151 of Alan C. Nelson, filed Aug. 10, 2001, that is in turn related to co-pending provisional application of Alan C. Nelson, Ser. No. 60/279,244, filed Mar. 28, 2001, both entitled "APPARATUS AND METHOD FOR IMAGING SMALL OBJECTS IN A FLOW STREAM USING OPTICAL TOMOGRAPHY." By this reference, applicant claims the benefit of the priority filing date of the co-pending provisional application.

FIELD OF THE INVENTION

The present invention relates to projection imaging systems in general and cell classification, and more particularly, to high throughput flow based automated systems using projection imaging, such as flow optical tomography (FOT), for detecting abnormal and malignant cells and for detecting rare cells based on highly quantative measurements of nuclear and cytoplasmic densitometric features (NDFs and CDFs) associated with disease.

BACKGROUND OF THE INVENTION

The most common method of diagnosing cancer in patients is by obtaining a sample of the suspect tissue and examining it under a microscope for the presence of obviously malignant cells. While this process is relatively easy when the anatomic location of the suspect tissue is known, it is not so easy when there is no readily identifiable tumor or pre-cancerous lesion. For example, to detect the presence of lung cancer from a sputum sample requires one or more relatively rare cancer cells to be present in the sample. Therefore, patients having lung cancer may not be diagnosed properly if the sample does not perceptively and accurately reflect the conditions of the lung.

One example of a microscope-based system and method for detecting diagnostic cells and cells having malignancy-associated changes is disclosed in Palcic et al., U.S. Pat. No. 6,026,174. The Palcic et al. system includes an automated classifier having a conventional microscope, camera, image digitizer, a computer system for controlling and interfacing these components, a primary classifier for initial cell classification, and a secondary classifier for subsequent cell classification. The method utilizes the automated classifier to automatically detect diagnostic cells and cells having malignancy-associated changes. However, the quality of the diagnostic result is limited by the use of a conventional microscope, which does not permit accurate measurement of stain densities. The method of Palcic et al. does not address the use of molecular probes.

With the advent of molecular probes, such as antibody probes and nucleic acid hybridization probes, new disease related questions can be addressed by tagging these molecular probes and then measuring their location and concentration within biological cells and tissues. As the need to more accurately localize and quantify these probes is emerging, there is a concomitant need for improved techniques to measure probe densities microscopically in two dimensions (2D) and three dimensions (3D). Conventional light microscopy, which utilizes cells mounted on glass slides, can only approximate 2D and 3D measurements because of limitations in focal plane depth, sampling angles, and problems with cell preparations that typically cause cells to overlap in the plane of the image. Another drawback of light microscopy is the inherent limitation of viewing through an objective lens where only the area within the narrow focal plane provides accurate data for analysis.

Flow cytometry methods generally overcome the cell overlap problem by causing cells to flow one-by-one in a fluid stream. Unfortunately, flow cytometry systems do not generate images of cells of the same quality as traditional light microscopy, and, in any case, the images are not three-dimensional. For background, those skilled in the art are directed to Shapiro, H M, *Practical Flow Cytometry*, $3^{rd}$ ed., Wiley-Liss, 1995.

In the area of computer aided tomography, U.S. Pat. No. 5,402,460, issued Mar. 28, 1995, to Johnson, et al. entitled "Three-dimensional Microtomographic Analysis System" discloses a microtomographic system for generating high-resolution, three-dimensional images of a specimen using an x-ray generator and an x-ray detector that measures the attenuation of the x-ray beam through the specimen. Two projections, each using a different energy x-ray beam, of each view of the specimen are made with Johnson, et al's microtomographic system. After the two projections of one view of the specimen are made, the specimen is rotated on the specimen holder and another set of projections is made. The projections of each view of the specimen are analyzed together to provide a quantitative indication of the phase fraction of the material comprising the specimen. The projections of the different views are combined to provide a three-dimensional image of the specimen. U.S. Pat. No. 5,402,460 is incorporated herein by reference. Although the x-ray technology as taught by U.S. Pat. No. 5,402,460 is useful for some applications, it does not provide an optical solution useful for flow cytometry, whereby one could measure the 3D distribution of molecular density within a biological cell.

To overcome the aforementioned limitations and others found in such systems, it is a motivation of this invention to combine the one-by-one cell presentation of flow cytometry with computational optical tomography from multiple point source projections to reconstruct density information within a cell from a plurality of projections. The reconstructed 3D density information enables the accurate measurement of nuclear densitometric features (NDFs) and cytoplasmic densitometric features (CDFs).

The NDFs and CDFs referred to herein are unique to projection imaging systems that do not require the use of lenses and focal planes with their inherent unwanted blur artifact due to unfocussed structures outside the narrow focal plane. Because projection imaging systems do not require lenses and focal planes, but rather, produce shadowgrams wherein all structures are in clear focus all at once, the measurement of density features will be more quantitative and accurate than in conventional microscopy systems. Therefore, the terms "NDF" and "CDF" refer to density feature measurements from shadowgrams and tomographic reconstructions using shadowgrams. NDFs and CDFs are subtle changes that are known to take place in cells associated with cancer tissue. These changes are indicative of deviation from normalcy and reflect molecular changes associated with the disease process.

However, NDFs and CDFs have not yet achieved wide acceptance for screening to determine whether a patient has or will develop cancer, because the methods of measurement have not provided adequate accuracy and/or throughput. Traditionally, NDFs and CDFs have been detected by carefully selecting a cell sample from a location near a tumor or pre-cancerous lesion and viewing the cells under a microscope using relatively high magnification. However, it is believed that the NDF and CDF changes that take place in the cells may be too subtle to be reliably detected by a human pathologist working with conventional microscopy equipment, especially because the pathologist is typically not making quantitative measurements. For example, an NDF change may be indicated by the distribution and density of DNA within the nucleus coupled with slight variations in the shape of the nucleus. Because human observers cannot easily quantify such subtle cell changes, it is difficult to determine which cells exhibit NDF alterations.

SUMMARY OF THE INVENTION

In one embodiment, the present invention provides a method for detecting cells of interest in a cell sample, comprising the steps of obtaining a cell sample and suspending the cells in solution; if required, fixing the cells of the cell sample in solution; staining and/or labeling the cells to generate optical densities associated with nuclear molecules or other structures within each cell of the sample; illuminating the sample with a "point" source of light and obtaining one or more projection images (e.g. shadowgrams) through the sample with a digital array detector; compensating the projection images for variations in background illumination; analyzing the projection images to detect objects of interest; calculating a set of one-dimensional (1D) and two-dimensional (2D) feature values for each object of interest; and providing the set of feature values to at least one classifier that identifies and characterizes cells of interest in the cell sample.

In another aspect, the present invention provides a system for automatically detecting NDFs and CDFs in cell samples. The preferred system includes a flow optical tomography (FOT) instrument that is controlled by and interfaced with a computer system. Projection images captured by the FOT are stored in an image processing board and manipulated by the computer system to detect the presence of one-dimensional and two-dimensional NDFs and CDFs. Multiple projection images can be reconstructed by the computer to generate three-dimensional (3D) and higher-dimensional (3D+) images with their associated NDFs and CDFs.

To measure the NDFs and CDFs, a cell sample is obtained and stained in suspension, and then imaged by the FOT. The stain is stoichiometric and/or proportional to DNA and/or its associated proteins or to other molecules of interest within the cell including the cytoplasm. The computer system then analyzes the projection images directly and/or computes the 3D reconstruction that is also analyzed. The images are corrected for uneven illumination and other imperfections of the image acquisition system. After all images are corrected, the edges, surfaces and volumes and densities of the objects of interest are calculated, i.e., the boundary that determines which pixels or voxels belong to the object or structure of interest and which belong to the background.

The computer system then calculates a set of 1D, 2D, 3D and 3D+ feature values for each object or structure. For some feature calculations the boundary along the highest gradient value is corrected by either dilating or eroding the edge (or surface) by one or more pixels (or voxels). This is done such that each feature achieves a greater discriminating power between classes of objects and is thus object specific. These feature values are then analyzed by a classifier that uses the feature values to determine whether the object is an artifact or is a cell nucleus or structure of interest. If the object appears to be a cell nucleus or structure of interest, then the feature values are further analyzed by the classifier to determine whether the object exhibits NDFs and CDFs indicative of disease. Based on the number of objects found in the sample that appear to have significant NDF and CDF disease related changes, a statistical determination can be made whether the patient from whom the cell sample was obtained is healthy or harbors a malignant growth.

In other embodiments, the present invention provides a method for detecting epithelial cells in a cell sample and a method for detecting cells having NDFs and CDFs that are correlated with disease among the epithelial cells. In another embodiment, a method for predicting whether a patient will develop cancer is provided.

DETAILED DESCRIPTION OF THE PREFERRED EMBODIMENTS

The invention is described herein with respect to specific examples relating to biological cells, however, it will be understood that these examples are for the purpose of illustrating the principals of the invention, and that the invention is not so limited. In one example, constructing a three-dimensional distribution of point densities and emission intensities within a microscopic volume allows the measurement of density and fluorescence at any location within the microscopic volume and determines the location of structures, molecules or molecular probes of interest. By using tagged molecular probes, the quantity of probes that attach to specific structures in the microscopic object may be measured. For illustrative purposes, an object such as a biological cell may be labeled with at least one tagged molecular probe, and the measured amount and location of this probe may yield important information about the disease state of the cell, including, but not limited to, various cancers such as lung, breast, prostate, cervical and ovarian cancers.

Biological cells that have been prepared for flow cytometry and stained or labeled with tagged molecular probes for specific disease diagnosis, are caused to flow through a device that provides for the collection of projection images and allows the reconstruction of 2D and 3D density information from optical projection ray paths approximately perpendicular to the flow vector of the cell. By controlling the velocity of the cell flowing along an axis, the perpendicular 2D planes of reconstruction can be correctly located (or stacked) along the axis of the cell to create a 3D picture of the entire cell, or a 3D image of the cell may be computed directly from 2D optical transmission or emission projections.

Flow cytometry is highly suitable for image reconstruction because of the following characteristics:

cells flow in single file through the capillary tube so cell overlapping and obscuration are minimized, the velocity of cells flowing through the capillary tube can be directly measured and is constant, cells tend to follow the center axis of the capillary tube and become structurally radially symmetric, and depending on the cell fixation and suspension preparation, cells can retain plasticity and assume an elongated shape along the z-axis in response to the velocity gradient in the capillary tube.

The present invention takes advantage of the aforesaid characteristics to provide a system for point source projection imaging and tomographic image reconstruction.

Figure 1:
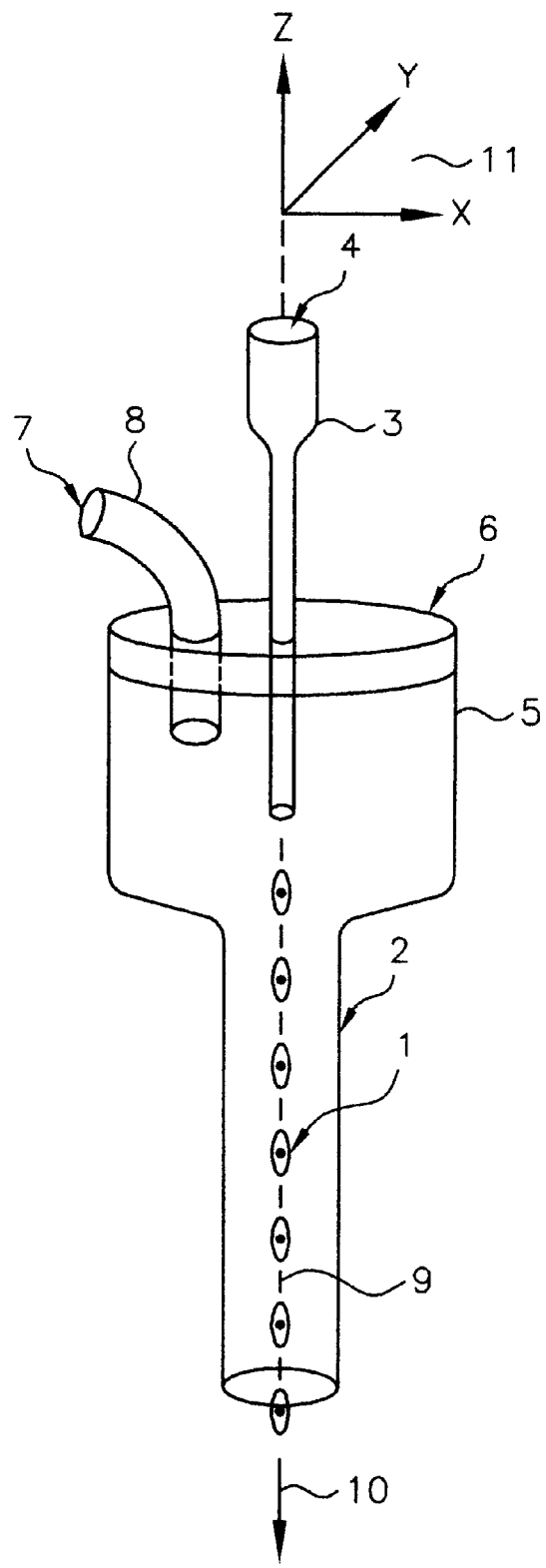
FIG. 1 schematically shows an example illustration of a flow cytometry system as contemplated by an embodiment of the present invention.

Referring now to FIG. 1, there shown schematically is an example illustration of a flow cytometry system as contemplated by an embodiment of the present invention. The system is oriented with reference to a coordinate system 11 having coordinates in the x, y and z-directions. In operation, cells 1 are injected into injection tube 3 using a known injection device 4. The capillary tube is wider at an injection end 5 and includes a pressure cap 6. A sheath fluid 7 is introduced at tube 8 to create laminar flow within the capillary tube 2. It is characteristic of traditional flow cytometry that the cells 1, prepared and suspended in solution, can be forced through a capillary tube 2 such that they elongate with the axis of flow and move approximately down the central axis of the capillary tube 2, as represented by dashed line 9. Cells may advantageously be made to flow with axial symmetry and with constant velocity 10 in single file along the center axis of a cylindrical capillary tube.

Figure 2:
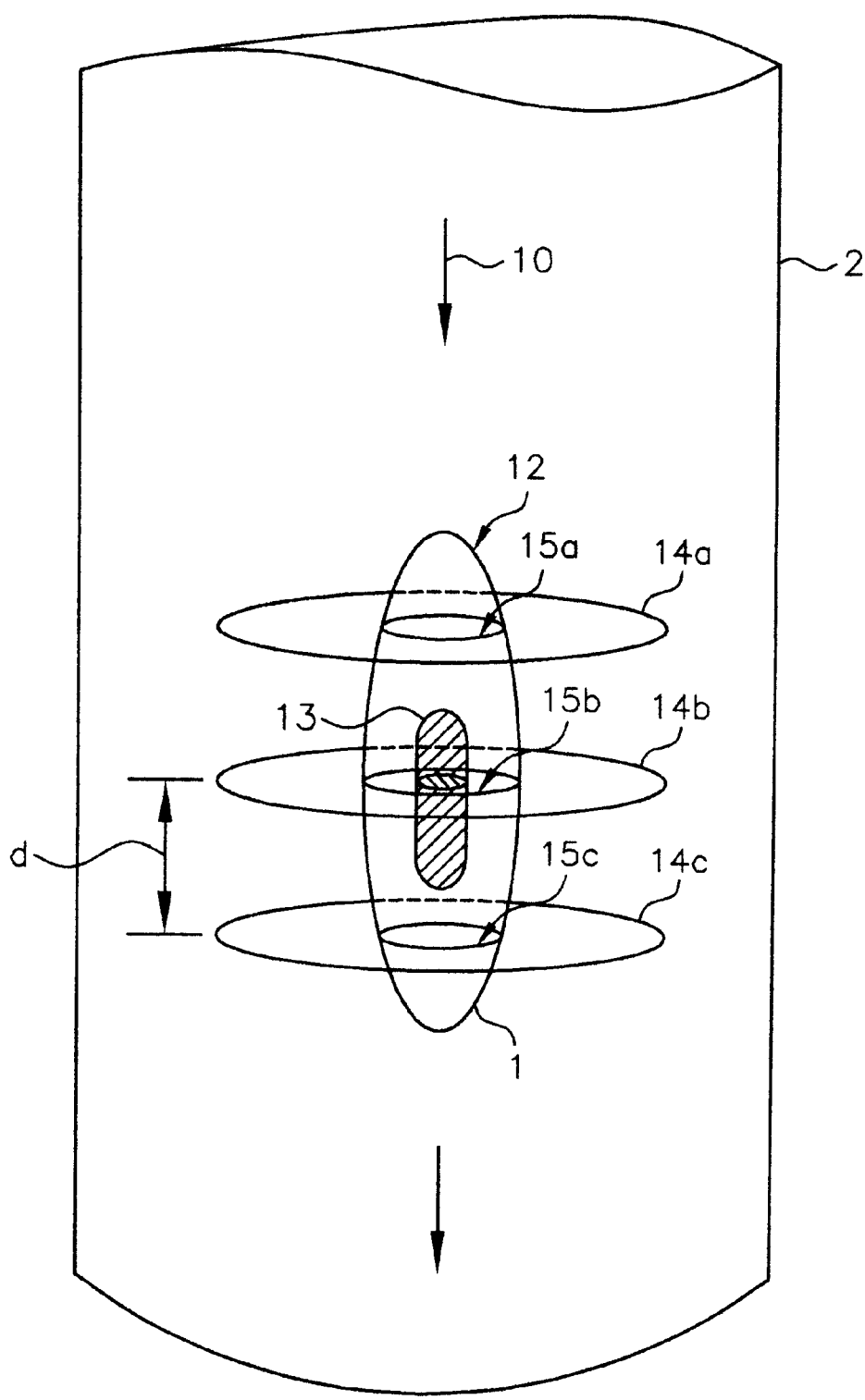
FIG. 2 schematically shows an example illustration of a flow process for a single cell as contemplated by an embodiment of the present invention.

Referring now to FIG. 2, there shown schematically is an example illustration of a flow process for a single cell as contemplated by an embodiment of the present invention. A cell 1 moves with a constant velocity (V) indicated by velocity vector 10 through a capillary tube 2. The cell 1 comprises a wall of cell cytoplasm 12 and a wall of cell nucleus 13. During the course of flowing through the capillary tube 2, the cell 1 passes through a plurality of reconstruction planes represented for illustrative purposes as first, second and third reconstruction planes 14a, 14b and 14c respectively. A first planar slice 15a through the wall of the cell cytoplasm lies within reconstruction plane 14a. Similarly, a second planar slice 15b through the walls of the cell cytoplasm and the cell nucleus, lies within the second reconstruction plane 14b, and a third planar slice 15c lies within the third reconstruction plane 14c. A central feature of the present invention is that a number of optical point sources of selectable wavelength are disposed about and concentric with the capillary tube. The optical point sources operate in conjunction with opposing optical sensor arrays that are sensitive to selectable portions of the light spectrum, thus allowing the acquisition of projections of the light transmitted through the cell. The acquired projection images may be analyzed directly or processed using tomographic image reconstruction algorithms to provide spatial maps or images of the distribution of densities and/or emission intensities within the cell. It will be understood that in practice the number of reconstruction planes may vary from several to several hundred or more, depending on the needed image resolution of the object being presented to the system. The group of reconstructed parallel planar slice images may be combined or stacked in software to produce a three-dimensional (3D) image of the densities and emission intensities within the cell. In addition, by employing planar (2D) instead of linear (1D) light sensor arrays, and a cone instead of a fan illumination ray pattern, projections of a plurality of contiguous planar slices through the flowing cells may be acquired simultaneously. As a result, three-dimensional (3D) images of the distribution of densities and emission intensities within the cell volume can be computed directly from the two dimensional (2D) projections using cone-beam reconstruction algorithms. Alternatively, the 2D point source projection images, which possess infinite depth of field, can be analyzed directly.

In the case of a biological cell, a distance (d) between reconstruction planes may be a few microns or less. A point within the cell 1 will coincide with each reconstruction plane at time intervals, where the time intervals (t) may be described according to the relationship:

$$t = d \div V \quad \text{(Equation 1)}.$$

Figures 3A, 3B:
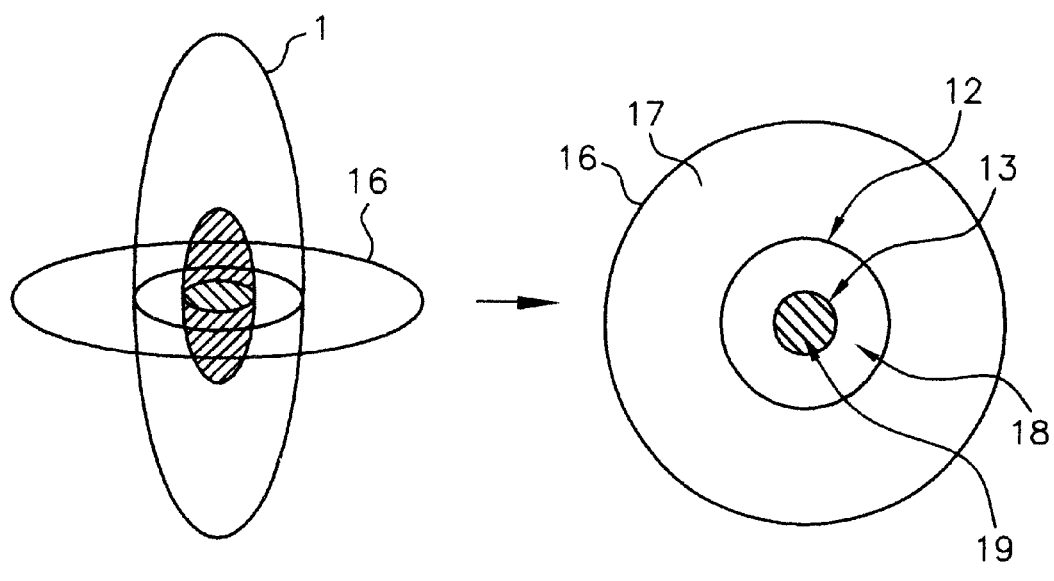
FIG. 3A and FIG. 3B schematically show an example of a cell and a cross-section of reconstruction as contemplated by an embodiment of the present invention.

Referring now jointly to FIG. 3A and FIG. 3B, there shown schematically is an example of a cross-section 16 of reconstruction as contemplated by an embodiment of the present invention. Reconstruction of point densities within a cell from optical projections through it benefits from the axial symmetry and centrality of the flowing cell. Additionally, the space being sampled by projections can be modeled as consisting of three discrete compartments:

1. the fluid outside the cell 17 (i.e. the sheath fluid or cell suspension medium),
2. the cell cytoplasm 18, and
3. the cell nucleus 19.

Knowing quantitatively the distribution of optical density or molecular probes in these three compartments is sufficient to address many important problems in cell biology and disease diagnosis. Additionally, it may be useful to compute two boundary surfaces including the cytoplasmic or cell wall 12 and the nuclear wall 13 if certain molecular probes bind preferentially to those surfaces. Otherwise, it may be sufficient to characterize these walls as the transition surfaces between the three different compartments.

By combining the reconstructed slices of the cell, or by reconstructing in a helical, volumetric manner, the 3D morphology and volume information can be generated, but absolute (as opposed to relative) volumes depend on accurate information of cell location. Cell location is a function of the flow velocity. However, in several instances, the relative concentrations of density or molecular probes are sufficient to address the diagnostic question: How much probe is in the cytoplasm relative to the nucleus vs. the non-bound probe in the background fluid? Or, is the probe located primarily on the cell membrane or nuclear membrane surface?

While the cells passing through the capillary tube may become structurally radially symmetric, the distribution within the nuclear and cytoplasmic compartments of at least one bound molecular probe may not possess such axial symmetry. It is therefore desirable for the imaging system and (particularly the emission) reconstruction algorithm to provide sufficient spatial resolution to localize volumes of bound, fluorescing molecular probe on a scale finer than that required to provide the three compartment analysis described above. It is further desirable that the system provides quantitative information about the concentration of asymmetrically distributed probe within the two intracellular compartments. The association of the probe with specific subcellular compartments, structures or organelles within the cytoplasm or nucleus is facilitated by submicron spatial resolution.

A more specific example pertains to the early detection of cancer in patients at risk. In such cases, certain genes may over or under express their function when the cell is undergoing transformation. It is diagnostically important to measure the relative over or under expression of the gene product (often a protein) in the cytoplasm relative to the nucleus, while normalizing for non-bound probes in the background suspension fluid. If the gene product is a protein, then a tagged antibody probe may be used to assess the disease state of the cell by localizing and/or quantifying the gene product protein. Hence, the three compartment analysis can be sufficient to make this the determination of disease state.

Figure 4:
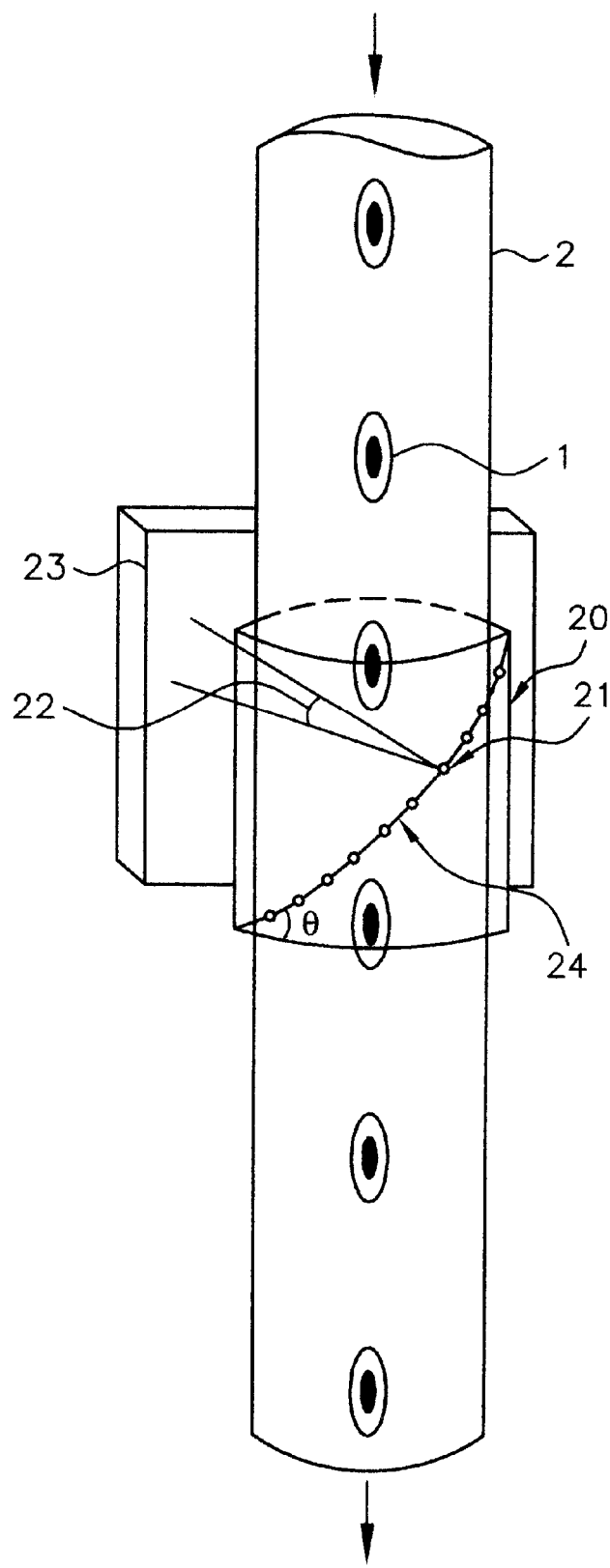
FIG. 4 schematically shows an example of a reconstruction cylinder as contemplated by an embodiment of the present invention.

Referring now to FIG. 4, there shown schematically is an example of a reconstruction cylinder, surrounding flow tube 2 containing flowing cells 1, as contemplated by an embodiment of the present invention. A reconstruction cylinder 20 includes, for example, a helix 24 of point sources 21 disposed at a predetermined helical pitch, with pitch angle θ. Each point source 21 generates a beam of photons 22, where the beam of photons 22 is typically cone or fan shaped. While the arrangement of the sources depicted in the example of FIG. 4 is helical, the array of point sources may take on a wide variety of geometric patterns, depending in part on the speed of the electronics, the cell velocity and the geometry that achieves non-overlapping projection signals at the sensor (detector). Sensing elements 23 are disposed to receive light from the point sources.

The fixed optical point sources 21, in conjunction with opposing detectors 23 mounted around a circumference of the tube can sample multiple projection angles through the entire cell 1 as it flows past the sources. By timing of the emission or readout, or both, of the light source and attenuated transmitted and/or scattered and/or emitted light, each detected signal will coincide with a specific, known position along the axis in the z-direction of the flowing cell. In this manner, a cell 1 flowing with known velocity along a known axis perpendicular to a light source that is caused to emit or be detected in a synchronized fashion, can be optically sectioned with projections through the cell that can be reconstructed to form a 2D slice in the x-y plane. By stacking or mathematically combining sequential slices, a 3D picture of the cell will emerge. It is also possible to combine the cell motion with the positioning of the light source (or sources) around the flow axis to generate data that can be reconstructed, for example, in a helical manner to create a 3D picture of the cell. Reconstruction can be done either by stacking contiguous planar images reconstructed from linear (1D) projections using fan-beam reconstruction algorithms, or from planar (2D) projections directly using cone-beam reconstruction algorithms. The 3D picture of the cell can yield quantitative measures of sub-cellular structures and the location and amount of tagged molecular probes that provide diagnostic information.

As mentioned, more than one projection through a cell section is required to reconstruct the 2D or 3D density structure in the section or volume. In traditional slice-by-slice medical x-ray computed tomography, multiple projections are made by holding the human patient motionless while the x-ray source and opposing detectors move along a circumference to generate multiple projection angles through the patient. By analogy, the flow optical tomography system of this invention moves the cell at a predetermined velocity (V) past multiple sources positioned at different angles along the circumference of the capillary tube to generate multiple projections through the cell as it flows past the point sources. These point sources emit photons that pass through the cell and are detected by an array of sensors opposite the source. The point sources can be arranged along a helix 24, or in other appropriate geometric patterns, on the circumference of the capillary tube such that each point in the cell is sampled from a multitude of angles as it passes through the array of point sources. For good sampling geometry, these point sources may cover at least 180 degrees of circumference. Less angular coverage (i.e. angular under sampling) may be feasible in some instances, while additional radial coverage will improve accuracy and the signal-to-noise ratio of the computed reconstruction. Depending on the geometry, it may be advantageous to apply traditional analytical, iterative or statistical algorithms for cone-beam or fan-beam image reconstruction. (See, for example, Gilbert, P, "Iterative Methods for the Three-dimensional Reconstruction of an Object from Projections," Journal of Theoretical Biology 36:105–17, 1972, Oppenheim, B E, "More Accurate Algorithms for Iterative 3 dimensional Reconstruction," IEEE Transactions on Nuclear Science NS-21:72–7, 1974, Singer, J R, Grunbaum, F A, Kohn, P, and Zubelli, J P, "Image Reconstruction of the Interior of Bodies that Diffuse Radiation," Science 248(4958):990–3, 1990. Mueller, K and Yage, R, "Rapid 3-D Cone-beam Reconstruction with the Simultaneous Algebraic Reconstruction Technique (SART) Using 2-D Texture Mapping Hardware", IEEE Transactions on Medical imaging 19(12):1227–37, 2001.) Related methods include, but are not limited to ART (algebraic reconstruction technique, as discussed in Bellman, S H, Bender, R, Gordon, R, and Rowe, J E, "ART is Science being A Defense of Algebraic Reconstruction Techniques for Three-dimensional Electron Microscopy," Journal of Theoretical Biology 32:205–16, 1971), SIRT (simultaneous iterative reconstruction technique, as discussed, for example by Gilbert, id. #1493), ML-EM (maximum likelihood expectation maximization, as discussed, for example, by Manglos, S H, Jaszcak, R J, and Floyd, C E, "Maximum Likelihood Reconstruction for Cone Beam SPECT: Development and Initial Tests," Physics in Medicine and Biology 34(12):1947–57,1989, #1382), and OSEM (ordered subsets expectation maximization, as discussed, for example, in Manglos, S H, Gagne, G M, Krol A, Thomas, F D, and Narayanaswamy, R, "Transmission Maximum-likelihood Reconstruction with Ordered Subsets for Cone Beam CT", Physics in Medicine and Biology 40(7):1225–41, 1995, #4389).

METHODS:

Flow Cytometer.

Figure 5:
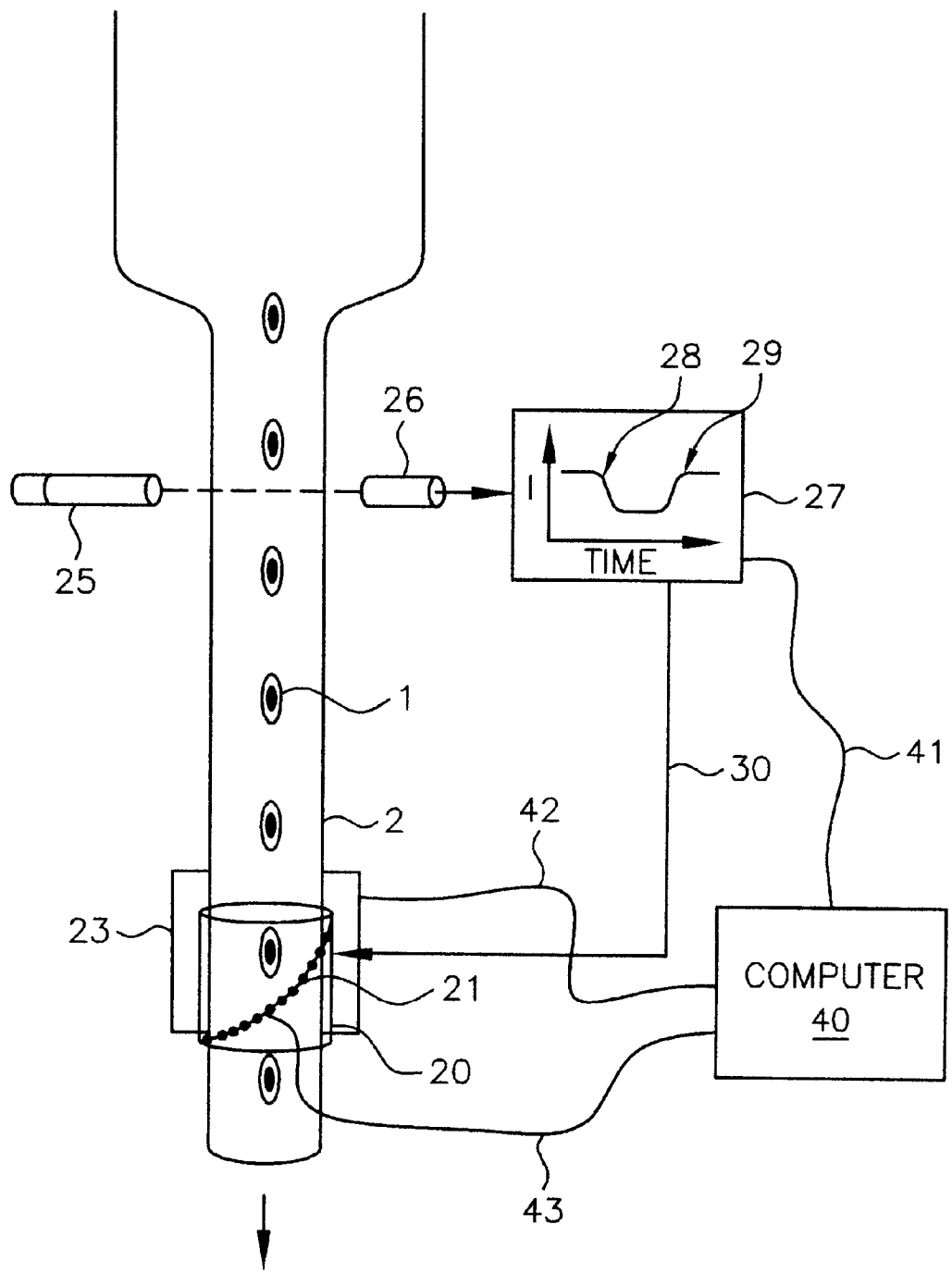
FIG. 5 schematically shows an example of a flow optical tomography (FOT) system as contemplated by an embodiment of the present invention.

Referring now to FIG. 5, there shown schematically is an example of a flow optical tomography system (FOT) as contemplated by an embodiment of the present invention. The flow optical tomography system includes a flow cytometer, with a reconstruction cylinder 20 positioned around capillary tube 2. A source of photons 25 and a photon sensor 26 work together with pulse height analyzer 27 to operate as a triggering device. Pulse height analyzer 27 operates in accordance with known principals to provide a first trigger point 28 for the beginning of a cell, and a second trigger point 29 for the end of the cell. The pulse height analyzer 27 outputs a trigger signal 30 corresponding to the beginning and end of each cell, where the trigger signal is received by the reconstruction cylinder 20.

A computer 40 is coupled to transmit data, control signals and timing signals to the point sources 21, sensing elements 23 and pulse height analyzer 27 by signal lines 41–43. The computer may comprise a known computer or plurality of computers and array processors adequate for image acquisition and image reconstruction processing.

Commercial flow cytometers come with three basic flow configurations: namely, the cylindrical flow tube, the rectangular flow tube and the flow in air system. (See Shapiro, H M, *Practical Flow Cytometry*, $3^{rd}$ ed., Wiley-Liss, 1995.) The preferred configuration is the cylindrical flow tube, because it is important to preserve optimal cylindrical geometry for the reconstruction algorithm to minimize any radial dependence due to the flow hardware (see FIG. 1). Moreover, the cylindrical flow tube may have uniformly thin walls relative to the cross-sectional area of the capillary tube.

Additionally, the triggering device may be located upstream from the reconstruction module to provide a timing signal to initiate then terminate data collection as the cell optimally enters then emerges from the reconstruction cylinder. The triggering device may advantageously comprise a laser diode, CCD, PMT, a photodetector combination, a solid state photodetector and combinations of the foregoing elements. The triggering device has a threshold setting that senses the presence of a flowing cell, thus generating a trigger signal that, in conjunction with a known cell velocity, can be used to calculate when the downstream reconstruction cylinder may commence data collection for that particular cell of interest. Further, the time interval between the first and second trigger points corresponding to the entrance and exit of the cell into and out of the reconstruction cylinder, may be divided into equal or unequal increments during each of which additional projection data may be acquired by strobing the light source(s) 21 and reading out the sensor array(s) 23.

The velocity of flow needs to be controlled and measured accurately. This capability is provided for in high-end commercial systems that use velocities in the range of 1 meter/sec to 10 meters/sec. The best cell velocity will be determined by the speed of data collection and signal-to-noise considerations as discussed subsequently.

The Reconstruction Module.

Figure 6:
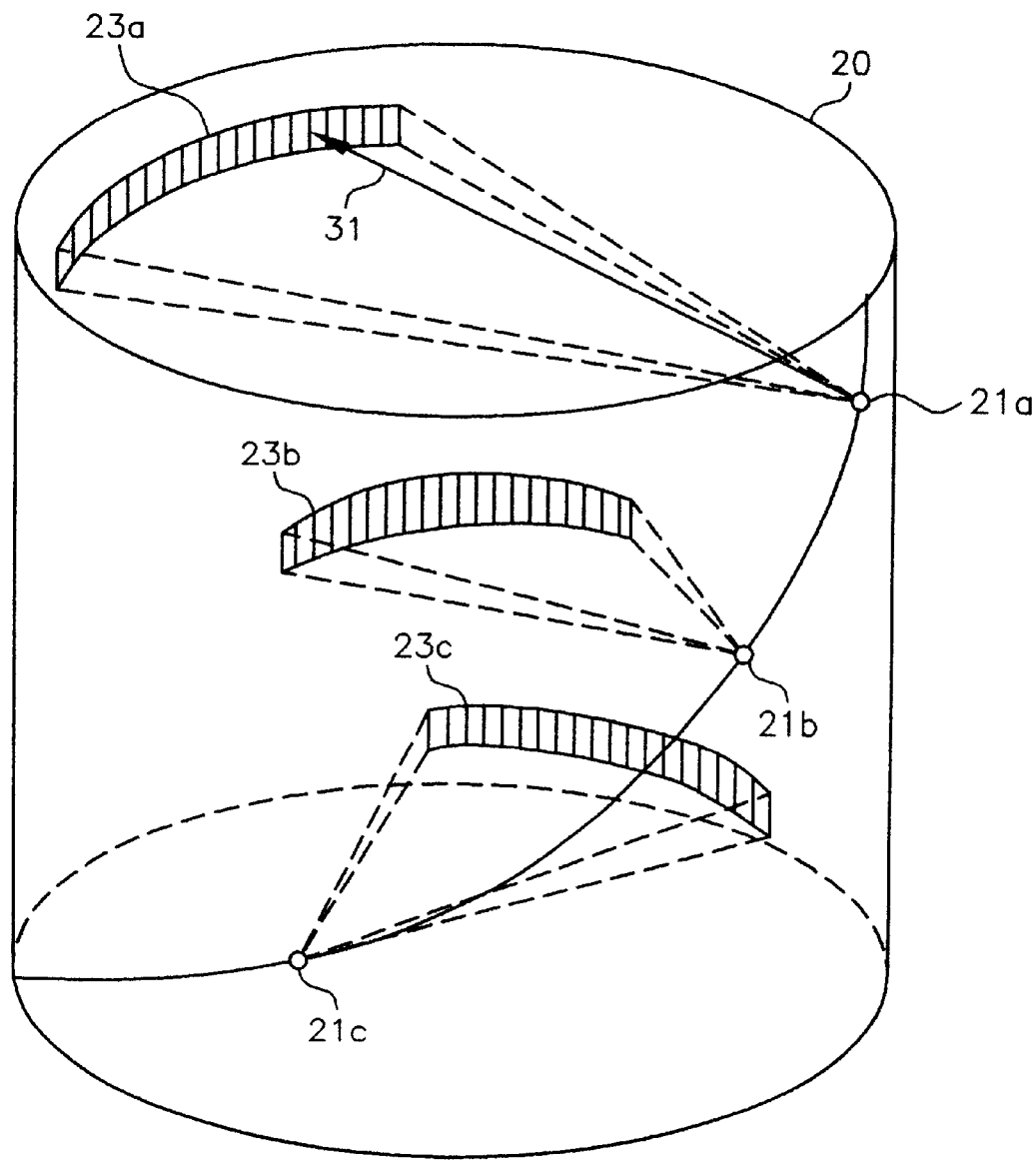
FIG. 6 schematically shows an example of projection rays within a reconstruction cylinder as contemplated by an embodiment of the present invention.

Referring now to FIG. 6, there shown schematically is an example of fan-beam projection rays within a reconstruction cylinder 20 as contemplated by an embodiment of the present invention. The purpose of reconstruction cylinder is to provide a means of projecting light from a plurality of fixed point sources 21*a*–21*c*, along a small circumference, into the cylindrical capillary tube. The photons emitted from the point sources have a known projection geometry, such as a fan or a cone shape, and pass through the capillary tube to be detected by an array of sensing elements 23*a*, 23*b* or 23*c*, as the case may be, located along a larger circumference opposite a corresponding point source. While curved linear (1D) sensor arrays suitable for fan-beam transillumination are depicted for purposes of illustration, it is to be understood that straight linear (1D) sensor arrays or planar (2D) sensor arrays suitable for cone-beam illumination may be similarly employed. In this manner, a set of projection rays can be generated where the projection rays can be described as the straight line connecting the point source to an individual sensing element. The difference between the number of photons leaving the point source along a particular projection ray, such as ray 31, and the number of photons received at the particular sensing element is related to the number of photons lost or attenuated due to interactions with the cell and other contents of the flow tube along the projection ray path.

However, complications may arise from light scatter, photon energy shifts, imperfect geometry and poor collimation, and photons from different sources may arrive at a particular sensing element when multiple point sources are energized simultaneously. With careful construction of the reconstruction cylinder, for example by judicious choice of the geometry for the pattern of point sources and their opposing detectors as described herein, and by proper timing or multiplexing of activation of the multiple point sources and readout of the sensor arrays, the photon contamination due to these issues can be minimized but not eliminated.

Photon contamination can be accounted for by calibration of the system, for example, with no cells present. That is, each light source may be illuminated in turn and its effects on each of the sensors can be measured, thereby providing offset data for use in normalizing the system. An additional calibration step may entail, for example, imaging latex polymer beads or other microspheres or oblate spheroids whose optical properties are known and span the density range of interest for cellular imaging. Photons emitted from fluorescing probes may be differentiated from those originating at the point sources by the use of spectral bandpass filters at the detector as discussed subsequently.

Light Source.

Each source may have the same general characteristics, preferably:

it may approximate a small circular point source, it may be bright with known spectral content, the photons emitted from the source may have a known geometry such as a cone-beam or a fan-beam.

Each source creates data for one projection angle. A plurality of sources arranged along a helix whose axis is the center axis of the flow tube creates data from multiple projection angles through each successive plane (or reconstruction slice) as the cell flows through the module. Depending on the sensor geometry, several point sources could be arranged co-linearly on the same circumference such that the projections do not overlap at the sensor. A good sampling geometry can be achieved by placing sources equidistant along a helix of 180 degrees, though less angular coverage may be tolerable in some instances, and 360 degrees may be employed to improve the signal-to-noise ratio. The desired number of sources is a function of the needed resolution within each planar reconstruction (the x-y plane) or volumetric reconstruction. While a helical arrangement of point sources is used for illustration, it is to be understood that a variety of geometric patterns may be employed for the point source array. Further, the wavelength of the sources is selectable either by use of various diode or other lasers or by bandpass filtering of a white or other broadband source, for example a mercury or xenon arc lamp.

Figure 7:
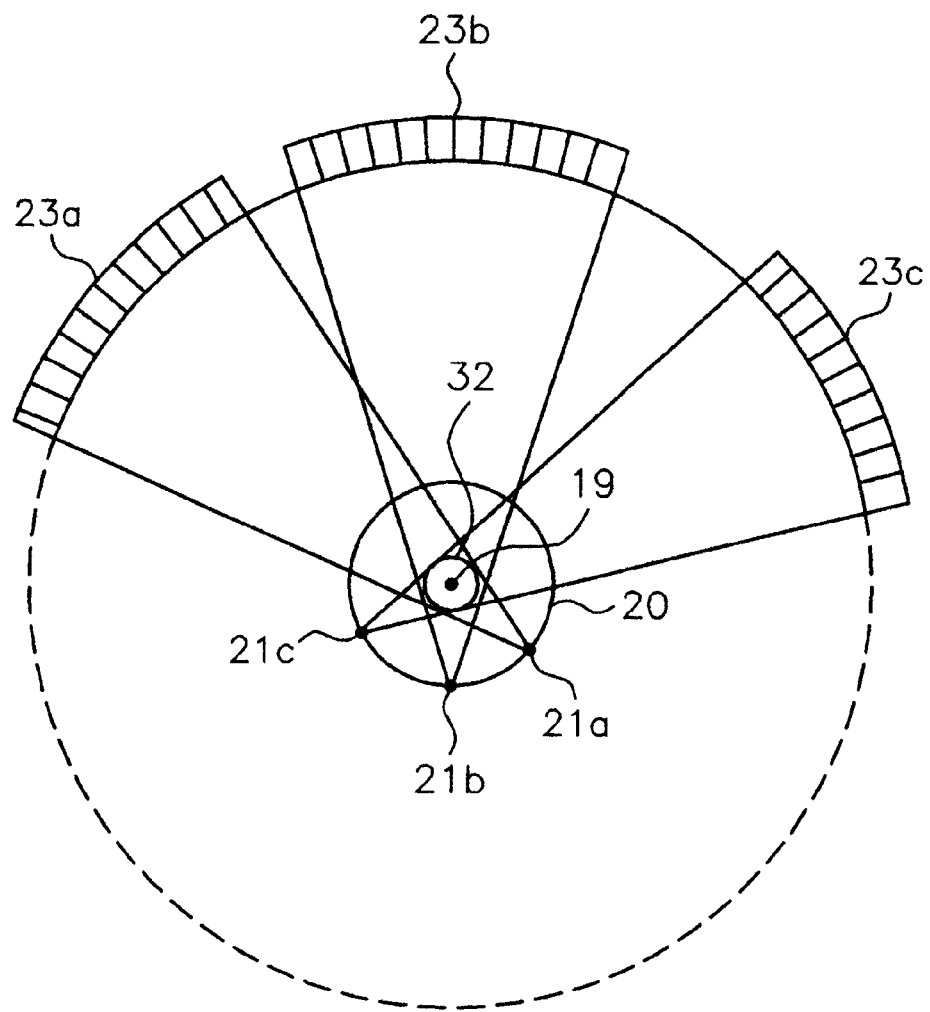
FIG. 7 schematically shows an example of a top view of a reconstruction cylinder as contemplated by an embodiment of the present invention.

Referring now to FIG. 7, there shown schematically is an example of a top view of a reconstruction cylinder, as shown in FIG. 6, as contemplated by an embodiment of the present invention. A first point source 21*a* and sensor array 23*a* are shown with a cell with nucleus 19 flowing perpendicular to the page in a projection of the source trajectory which, in two dimensions, constitutes a circle of reconstruction 32, in which all projections, even though acquired in a temporally staggered fashion, are depicted as overlapping, and in which the whole cell is contained. A second point source 21b and second sensor array 23b are located about 30° around the helix. A third point source 21c and third sensor array 23c are located about 90° around the helix.

Data collection is gated in synchrony with the cell velocity within a "thick" planar axial cross-section of the cell. The desired plane thickness is a function of the needed resolution in the z-direction. Typically, the resolution in the axial (z-direction) will be less than in the planar transaxial direction. Also, the best circle of reconstruction may be defined by the overlapping intersection of the projection fans having the point sources at their apexes and the width of the sensing arrays at their bases. It is desirable that the geometry of the reconstruction cylinder assures that the flowing cell cross section is contained entirely within the circle of reconstruction.

There are several options that can be employed to create optical point sources, such as:

a pinhole in front of a laser or other high intensity photon source, an optical fiber with a small cross-section, a short focal length lens in front of a photon source, an electron beam that irradiates a point on a phosphor surface (a form of CRT), and various combinations of the above.

The geometry is such that the closer the point source to the object of interest (the cell) the higher the magnification due to the wider geometric angle that is subtended by an object closer to the source. Conversely, if the required resolution is known in advance of the system design, then the geometry can be optimized for that particular resolution. For background, those skilled in the art are directed to Blass, M, editor-in-chief, *Handbook of Optics: Fiber Optics and Nonlinear Optics*, $2^{nd}$ ed., Vol. IV, Mcgraw-Hill, 2001.

Figure 8:
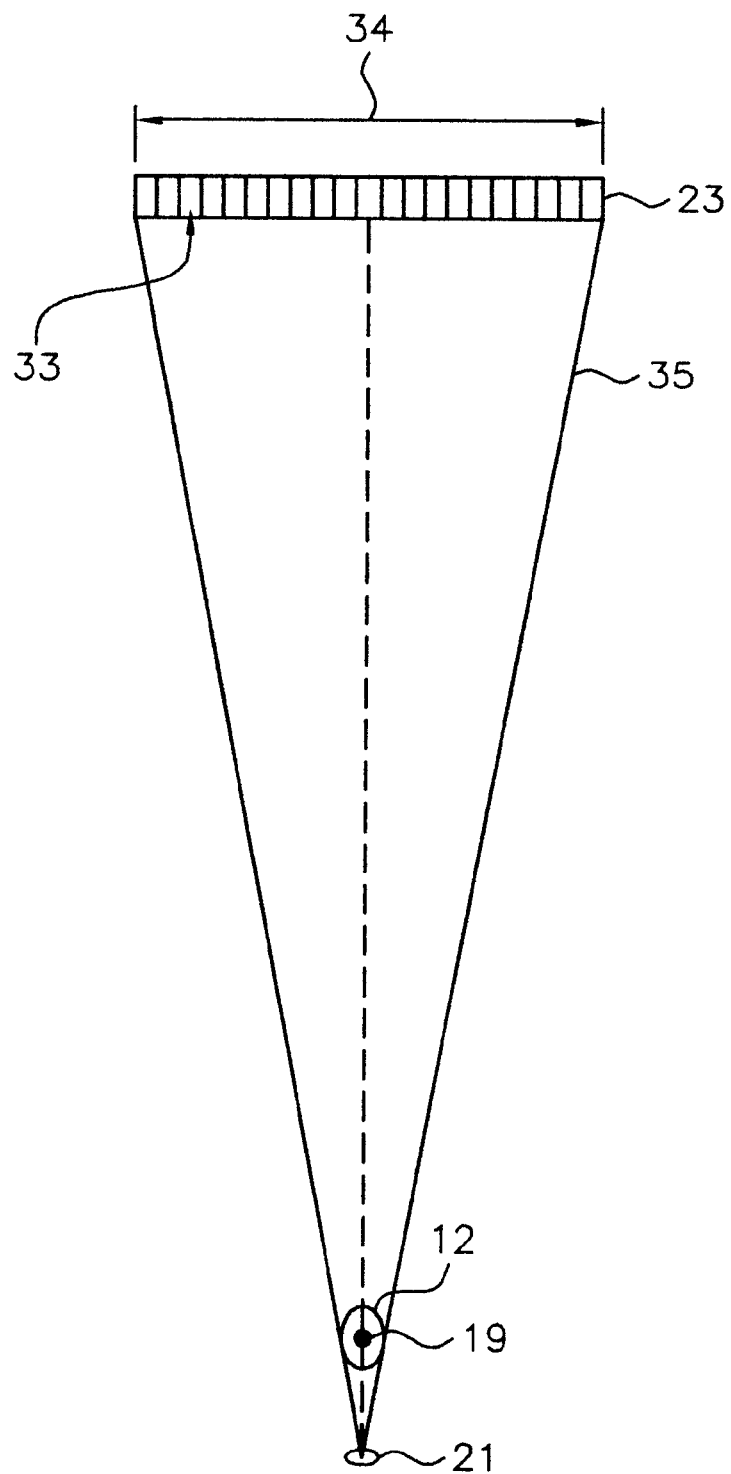
FIG. 8 schematically shows an example of the geometry of a source/linear array configuration used in cell reconstruction as contemplated by an embodiment of the present invention.

Referring now to FIG. 8, FIG. 8 schematically shows an example of a straight linear array 23 used in cell reconstruction as contemplated by an embodiment of the present invention. For example, given a cell cross section 12 and nucleus 19 contained within a 30-micron diameter circle of reconstruction and a desired resolution of 0.5 microns, then Nyquist sampling (i.e. over-sampling by a factor of two) dictates that at least 120 sensing elements 33 are required for each point source 21. The point source 21 at the apex and the linear array length 34 at the base form a triangle 35, such that the example 30-micron diameter cell fits within the triangle 35 as closely as possible to the point source 21. In this example, if each element of the (e.g. CCD) array is 20 microns wide and the array length is 2400 microns, then the center of the cell may be located about 100 microns (half the diameter of the capillary tube) from the point source when the distance between the point source and the linear array is 8 millimeters, providing 80-fold magnification.

As a second example, consider a 30-micron diameter circle of reconstruction and a complementary metal oxide semiconductor (CMOS) sensing array in which the pixel element size is 4 microns. In this case the array may contain 120 elements for a width of 480 microns, and it may be positioned 1.6 mm from the point source when the distance between the point source and the cell is 100 microns, providing a 16-fold magnification.

Sensing Elements

Each point source shall have a corresponding array of sensing elements such as CCDs in some straight or curved geometric arrangement opposite the point source to receive photon rays transmitted through the circle of reconstruction. Typically, the linear array may have its array of sensing elements centered on the line between the point source and the central flow axis, and may line up perpendicularly to the flow axis. It is possible to use 2D arrays where only a subset of each line of elements within the 2D array is read out for the reconstruction input. In a 2D array, each successive subset of elements may be staggered by the appropriate number of elements to align properly with each different point source along the helical arrangement of point sources.

For slice-by-slice fan-beam reconstruction using the example of the 30-micron reconstruction circle with 120 sensing elements per fan to obtain a resolution of 0.5 microns, a 2D array with 2000×2000 20-micron elements is sufficient for sensing 136, point sources arranged at 1 radial degree increments, where the average off-set between successive views is 300 microns, where that is equivalent to 15 sensing elements. (At the center of the array, the offset may be 140 microns, or 7 elements, while at the edges of the array, a 1 radial degree sweep between views may entail a considerably larger offset.) If groups of 15 rows of the sensor array were averaged to provide the projection data for one slice, the z-resolution within the cell image may be 3.75 microns, whereas if 2 rows were averaged for each projection, the axial resolution in object space may be 0.5 microns, equivalent to the transaxial resolution.

In a preferred embodiment of the invention, the 2D array is curved along a cylindrical circumference that may be concentric with the reconstruction cylinder, so that the ray paths are all equal in length. For the case of a 30-micron reconstruction circle, a curved, 2D array that possessed only the elements required to oppose a helical locus of point sources may be a helical strip 120 elements wide by some multiple of 136 elements in height (length) for the example described above.

Though planar or "thick" fan illumination is described for purposes of the illustration above, it is to be understood that true, uncollimated cone-beam illumination may be employed in conjunction with 2D planar detectors, providing for 3D reconstruction using cone-beam algorithms. The 2D projection images may be analyzed directly to obtain, for example, information about the disease status or transformation state of the cell. For direct, volumetric cone-beam reconstruction, the illumination from a plurality of point sources is multiplexed in such a way that, given the geometric arrangement of the point sources and detectors, the cones of illumination from different point sources do not overlap on the sensor array.

Moreover, if the cell were flowing with a velocity of 1 meter/sec (or 1,000,000 microns/sec) and each element in the 2D array were 20 microns wide, then a line read-out every 20 microseconds may readily capture data within a 0.25-micron slice of the cell. For the case when 15 sensor rows are averaged to provide the data for a 3.75-micron slice, readouts would have to occur every 300 microseconds. A significant improvement in reconstruction image quality is achieved using a larger 2D array.

One embodiment of the present invention especially suited for multispectral imaging of a number of transmitted or emitted wavelength bands may advantageously include two or more reconstruction modules arranged in series. Such multiple reconstruction cylinders may be separated by intervening sections of capillary tube, and each module provides projection data adequate to produce a complete reconstructed image of the objects flowing through it. The point sources and/or sensor arrays for each of the several reconstruction modules may be optimized for a particular spectral band. For example, a first reconstruction module may employ intense white light illumination and unfiltered detection to provide a complete projection data set to reconstruct a map of object optical density, absorption or scattering coefficients, while a second reconstruction module may employ illumination, such as an argon-ion laser (488 nm), in a narrow spectral band centered around 495 nm to excite fluorescing probe labeling proteins for an immunofluorescence study in conjunction with filtered sensor arrays sensitive to the 520-nm emission to provide a second complete projection data set sufficient to map the concentration distribution of the labeled proteins by using emission reconstruction algorithms, as described subsequently. Yet a third reconstruction module may use narrow-band illumination centered around 535 and/or 342 nm to excite propidium iodide bound stoichiometrically to DNA and filtered sensor arrays to optimally detect the red (617-nm) emissions for studies of ploidy. It will be understood that the aforesaid examples are for illustrative purposes, and that the method applies generally to any wavelength combinations for illuminating and sensing.

Image Reconstruction.

The most common and easily implemented reconstruction algorithms, known as filtered backprojection methods, are derived from a similar paradigm in computerized x-ray tomography (CT) using cone-beam and fan-beam geometry. (See the following references, for example, Kak, A C and Slaney, M, *Principles of Computerized Tomographic Imaging*, EEE Press, New York, 1988, and Herman, G, *Image Reconstruction from Projections: The Fundamentals of Computerized Tomography*, Academic Press, New York, 1980.) These methods are based on theorems for Radon transforms with modifications that reflect the particular geometry of the source/detector configuration and the ray paths in the irradiating beam. However, in the case of clinical x-ray CT, for slice-by-slice acquisition, the human subject is usually held motionless while the x-ray source and detector arrays may move along an arc around the patient to collect data from multiple projection angles within a given slice. Then the human subject is repositioned along the z-axis and another slice of data is collected, etc. Alternatively, in the more modern clinical helical CT, the patient may be continuously translated in the z-direction while the source-detector assembly rotates continuously to provide helical projection data, which is then interpolated to provide projections orthogonal to the patient z-axis. In flow optical tomography, the subject (a cell) is moved with constant velocity relative to the stationary sources and detector arrays wherein the plurality of source/detector systems acquire data in synchrony with specific gated time points along the cell velocity vector in a fashion that generates multiple projection angle data within a given slice or volume. For slice-by-slice scanning, the reconstruction algorithm will compute a 2D image of a plane perpendicular to the axis of motion, and the serial stacking of multiple slices will generate the 3D picture of the subject where contrast is a function of the variations in the x-ray attenuation coefficient or optical density within the subject for CT or flow optical tomography, respectively. For volumetric, cone-beam scanning the reconstruction algorithm computes a 3D image of a volume within the cell or other object directly from planar transmission or emission optical projections, where the contrast is a function of the optical density and/or tagged probe density distribution, respectively, within the imaged object.

It may be desirable for either the transmission data to produce the cell density reconstruction or for the emission data to reconstruct the labeled probe distribution, or both, to employ image reconstruction algorithms other than filtered backprojection. The general class known as iterative reconstruction algorithms is more efficacious in some instances, especially for emission tomography or when it is possible, as in the instance of the current invention where the axial symmetry and tricompartmental nature of the object are known, to incorporate a priori information into the reconstruction algorithm to improve the quality of the reconstruction(See, for example, Gilbert, P, "Iterative Methods for the Three-dimensional Reconstruction of an Object from Projections," Journal of Theoretical Biology 36:105–17, 1972, and other references noted hereinabove).

Similarly, one method may advantageously use finite element modeling-based (FEM), statistical reconstruction algorithms. FEM algorithms are derived from linear transport theory in which the photon diffusion/migration equation is solved at all the boundaries of the elements to produce a two- or three-dimensional map of some combination of the absorption, scattering, refractive index and anisotropy factor properties of the imaged object. Examples of such methods are taught in Paulsen, KD and Jiang, H, "Spatially Varying Optical Property Reconstruction Using a Finite Element Diffusion Equation Approximation", Medical Physics 22(691–701) 1995, Hampel, U and Freyer, R, "Fast Image Reconstruction for Optical Absorption Tomography in Media with Radially Symmetric Boundaries", Medical Physics 25 (1):92–101, 1998, and Jiang, H, Paulsen, K D, and Osterberg, U L, "Frequency-domain Near-infrared Photo Diffusion Imaging: Initial Evaluation in Multitarget Tissuelike Phantoms", Medical Physics 25(2):183–93,1998.

Chromatic Separation.

If a polychromatic point source is used (e.g., white light) then different chromatic stains (e.g. chromaphors) can be utilized to distinguish a number of molecular probes and structural features within a given cell. Here, serial bandpass filters at the source or sensing array (or both) separate the wavelength data and allow the reconstruction and spatial localization of the individually stained molecules. A more robust method for imaging multiple probes involves an intense white light source and simultaneous collection of multiple filtered bandwidths in the sensor arrays thus allowing the image reconstruction algorithms to compute spatial image slices for each chromaphor. These may be displayed as colored images.

Fluorescence, Phosphorescence, Chemiluminescence and Nano-Particle Emission

As a special case of the flow optical tomography system, certain molecular probes can be tagged with a "reporter" that emits light of a different (longer) wavelength when stimulated by the primary source of photons. The secondary emission from the reporter can be filtered with standard optical filters to separate the primary source photons from the secondary emission photons. However, the secondary emission photon image reconstruction algorithm is further complicated, because the secondary photons do not necessarily arise in a direct ray path from the point source. If it is assumed that the secondary photons radiate from the secondary point source in a uniform spherical pattern, then the intensity of the secondary photons reaching any sensing element will be a simple function of distance to the sensing element. A further refinement may account for the non-spherical distribution of photons from the secondary source by providing a model of the spatial distribution of secondary photons relative to the point source and within the reconstruction slice. Either method will provide a means to calculate the location of the secondary source in the reconstruction slice or volume. Collimation between the imaged object and the detector array(s) will improve the image reconstruction.

If the primary photon intensities and the secondary photon intensities are measured simultaneously by optical filtration, the high resolution density reconstruction from the primary photon intensities can be superimposed upon or fused with the secondary source reconstruction such that image morphology along with localized probe concentration is available in a single reconstructed image. Depending on intensity, signal-to-noise and on the ability to filter or produce narrow bandwidths of photons at the source and/or sensors, it may be advantageous to utilize multiple secondary sources each corresponding to a different tagged molecular probe.

U.S. Pat. No. 6,201,628 entitled "High Throughput Optical Scanner", issued Mar. 13, 2001, to Basiji, et al. discloses a scanning apparatus provided to obtain automated, rapid and sensitive scanning of substrate fluorescence, optical density or phosphorescence. The scanner uses a constant path length optical train, which enables the combination of a moving beam for high speed scanning with phase-sensitive detection for noise reduction, comprising a light source, a scanning mirror to receive light from the light source and sweep it across a steering mirror, a steering mirror to receive light from the scanning mirror and reflect it to the substrate, whereby it is swept across the substrate along a scan arc, and a photodetector to receive emitted or scattered light from the substrate, wherein the optical path length from the light source to the photodetector is substantially constant throughout the sweep across the substrate. The optical train can further include a waveguide or mirror to collect emitted or scattered light from the substrate and direct it to the photodetector. For phase-sensitive detection the light source is intensity modulated and the detector is connected to phase-sensitive detection electronics. A scanner using a substrate translator is also provided. For two dimensional imaging the substrate is translated in one dimension while the scanning mirror scans the beam in a second dimension. For a high throughput scanner, stacks of substrates are loaded onto a conveyor belt from a tray feeder. U.S. Pat. No. 6,201,628 is incorporated herein by reference. However, neither of these patents allows for the generation of optical projection images, and consequently, tomographic reconstruction is not possible without such images.

As described above, the present invention is a system for automatically detecting NDFs in the nuclei and CDFs in the cytoplasms from optical projections and tomographic reconstructions of cells obtained from a patient. From the presence or absence of disease related NDFs and CDFs, a determination can be made whether the patient has a malignant cancer.

Figure 9:
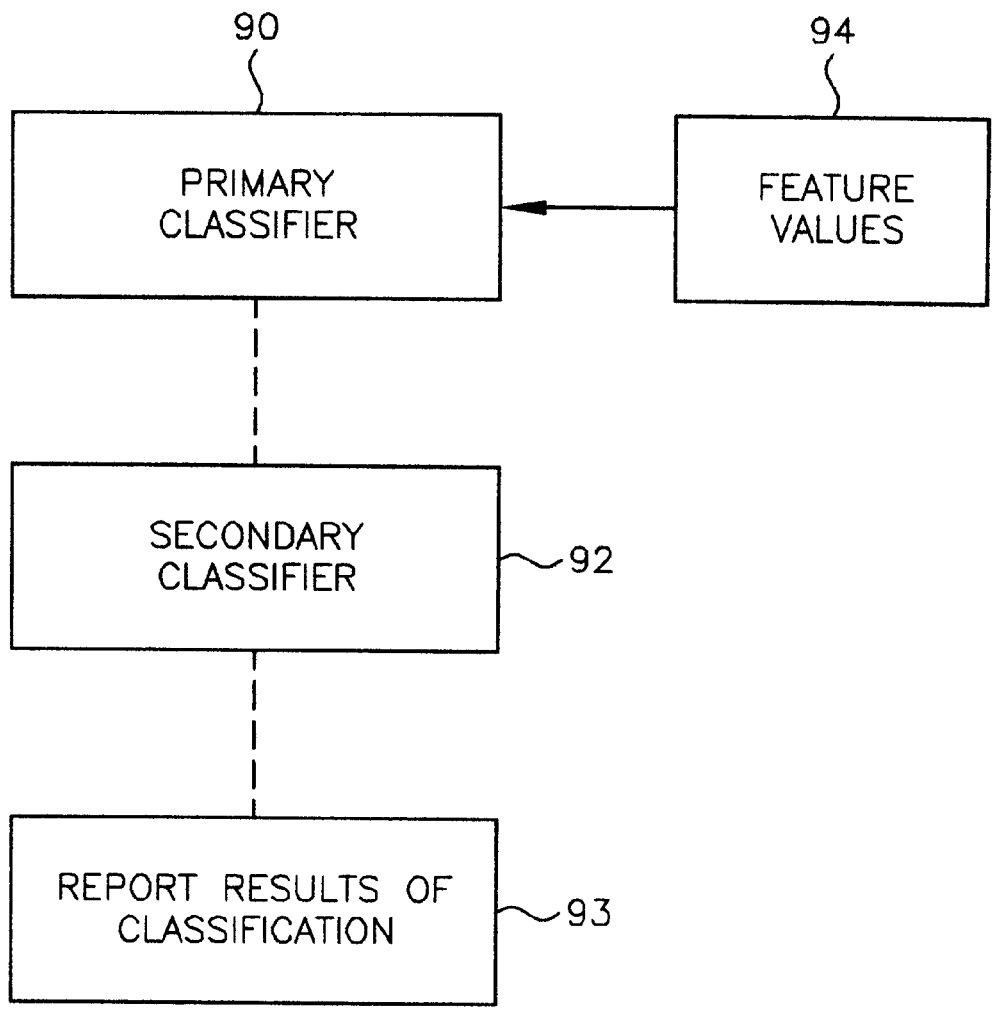
FIG. 9 schematically shows an example of a classification method used in the analysis of NDFs and CDFs from projection images and tomographic reconstruction as contemplated by an embodiment of the present invention.

Referring now to FIG. 9, there shown schematically is an example of a classification method with cell reconstruction data as contemplated by an embodiment of the present invention. The system may include several classifiers that can work together to determine whether a particular cell sample contains cells of interest and diagnostic cells having NDFs and CDFs associated with disease. A classifier is a computer program that analyzes an object based on certain feature values 94. The automated classifier system of the present invention may include, for example, a primary classifier 90, which performs a basic screening function, and selects objects of interest. A secondary classifier 92 classifies cellular objects as morphologically abnormal or morphologically normal and having NDFs and CDFs associated with disease, or normal and not exhibiting disease related NDFs and CDFs. A report 93 may be provided detailing the classification results of any one or all of the classifiers. It will be understood that many and various classifiers may be employed. Depending upon the application.

As noted above, while the automated system of the present invention may include a primary and secondary classifier, a single classifier can be used to sequentially obtain the classifications achieved by the present invention. The software packages used to generate classification functions based on statistical methods are generally commercially available.

The automated classifier of this invention preferably includes classifiers that utilize fuzzy binary decisions or Bayesian statistical decisions based on directly calculated NDFs and CDFs in performance of their classification function. The classifier can be constructed to include a large number of feature values, for example, including the morphological features, photometric features, discrete texture features, Markovian texture features, non-Markovian texture features, fractal texture features and run length texture features.

The primary classifier may typically function to subtype objects of interest into three classes: (1) epithelial cells including diagnostic cells and cells that may contain NDFs and CDFs associated with disease; (2) inflammatory cells; and (3) artifacts. The primary classifier can affect cell-by-cell classification through a binary decision tree incorporating a selection of feature values.

As indicated above, the ability of the system of the present invention to distinguish cell nuclei from artifacts, epithelial cells from other cell types, and cells having NDFs and CDFs associated with disease from other normal epithelial cells depends on the ability of the classifier to make distinctions based on the values of the features computed. For example, to distinguish normal epithelial cells from abnormal epithelial cells (i.e., diagnostic cells), the present invention may apply several different discriminant functions, each of which is trained to identify particular types of objects and particular changes in NDFs and CDFs.

The secondary classifier classifies the epithelial cells in the cell sample selected by the primary classifier and also uses a binary decision tree and feature values in performance of its classification function. The secondary classifier, which can be considered as a sample-by-sample classifier, analyzes the epithelial cells classified by the primary classifier and classifies those cells as normal and disease NDF or CDF-negative or normal and disease NDF or CDF-positive. As with the primary classifier, the secondary classifier is constructed to distinguish cells based on a set of preferred NDF and CDF features.

The feature sets used by each classifier are developed from discriminant functions analyzing the quantitative density features of cell nuclei and/or cytoplasm and, preferably, include a minimum number of features. Ideally, the selection of a minimum number of optimal nuclear features results in an efficient and robust classifier. That is, a classifier is preferably both efficient in accurately classifying a cell or a cell type, and robust in reliably classifying a variety of cell and sample preparations.

The classifier may include at least one discriminant function, wherein the discriminant function uses features from shadowgrams to classify cells of interest in the sample including, but not be limited to, 1D and 2D nuclear densitometric features (NDFs) and cytoplasmic densitometric features (CDFs) and features selected from the group consisting of area, mean radius, optical density (OD) variance, OD skewness, OD range, OD average, OD maximum, density of light spots, low DNA area, high DNA area, low DNA amount, high DNA amount, high average distance, mid/high average distance, correlation, homogeneity, entropy, fractal dimension, DNA index, texture, punctateness, connected components and the various harmonics in spatial density frequency space.

The cell sample may be a human lung specimen, a human cervical specimen, a blood specimen, or may contain rare cells. In one example, the staining of a sample to identify NDFs and CDFs comprises staining with a stoichiometric or proportional DNA and RNA stain. The DNA stain may be selected from the group consisting of Feulgen stain, Romanowski stain, May-Grunwald-Giemsa stain, Methyl Green and thionin 9. In another example, the sample may be stained with an antibody marker to identify NDFs and CDFs. In another example, a nucleic acid sequence marker may advantageously be used to stain the sample.

The system of the invention is useful for analyzing various types of biological cells. In one example, the cell of interest can be selected to be diagnostic of cancer, and/or, the cell of interest may advantageously be a preinvasive cancer cell. The cell of interest may comprise an invasive cancer cell where the cells of interest are utilized in screening a patient for cancer. The cells of interest may also be utilized in determining whether a patient will develop invasive cancer. The invasive cancer cell can be derived from an epithelial cancer. Alternatively, or in addition, the preinvasive cancer cell can be derived from an epithelial cancer. The epithelial cancer may be advantageously selected from the group consisting of lung and throat cancer, cervical and ovarian cancer, breast cancer, prostate cancer, skin cancer and cancer of the gastrointestinal tract.

In an embodiment used to analyze multi-dimensional images, such as, for example, 3D images and higher-dimensional (3D+) images, the features used to classify cells of interest in the sample may comprise, but are not limited to, 1D, 2D, 3D and 3D+ nuclear densitometric features (NDFs) and cytoplasmic densitometric features (CDFS) and features selected from the group consisting of area, mean radius, volume, mean volume, optical density (OD) variance, OD skewness, OD range, OD average, OD maximum, density of light spots, low DNA volume, high DNA volume, low DNA amount, high DNA amount, high average distance, mid/high average distance, correlation, homogeneity, entropy, fractal dimension, DNA index, texture, punctateness, connected components and the various harmonics in spatial density frequency space. High DNA volume, for example, may be that which is above a baseline as measured in a population of normal cells.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

What is claimed is:

1. A method for detecting cells of interest in a cell sample, comprising the steps of:
   (a) obtaining a cell sample and suspending the cells in solution;
   (b) if required, fixing the cells of the cell sample in solution;
   (c) marking the cells to generate optical densities within each cell of the sample;
   (d) illuminating the sample with at least one point source of light;
   (e) obtaining at least one projection image through the sample with a digital array detector;
   (f) compensating the at least one projection image for variations in background illumination;
   (g) analyzing the at least one projection image to detect at least one object of interest;
   (h) calculating a set of feature values having one-dimensional (1D) feature values and two-dimensional (2D) feature values for the at least one object of interest;
   (i) providing the set of feature values to at least one classifier; and
   (j) using the set of feature values and the at least one classifier for identifying the at least one object of interest from the cell sample.

2. The method of claim 1, wherein the set of feature values used to classify the at least one object of interest in the sample are selected from the group consisting of 1D and 2D nuclear densitometric features (NDFs), cytoplasmic densitometric features (CDFs), area, mean radius, optical density (OD) variance, OD skewness, OD range, OD average, OD maximum, density of light spots, low DNA area, high DNA area, low DNA amount, high DNA amount, high average distance, mid/high average distance, correlation, homogeneity, entropy, fractal dimension, DNA index, texture, punctateness, connected components and harmonics in spatial density frequency space.

3. The method of claim 1, wherein the step of using the at least one classifier comprises using a classifier having at least one discriminant function.

4. The method of claim 3 wherein the at least one discriminant function uses a set of discriminant features selected from the group consisting of 1D and 2D nuclear densitometric features (NDFs), cytoplasmic densitometric features (CDFs), area, mean radius, optical density (OD) variance, OD skewness, OD range, OD average, OD maximum, density of light spots, low DNA area, high DNA area, low DNA amount, high DNA amount, high average distance, mid/high average distance, correlation, homogeneity, entropy, fractal dimension, DNA index, texture, punctateness, connected components and harmonics in spatial density frequency space.

5. The method of claim 1 wherein the cell sample comprises a human lung specimen.

6. The method of claim 1 wherein the cell sample comprises a human cervical specimen.

7. The method of claim 1 wherein the cell sample comprises a human blood sample.

8. The method of claim 1 wherein the cell sample comprises rare cells.

9. The method of claim 1 wherein the step of marking the sample comprises staining with a stain selected from the group consisting of stoichiometric DNA stain, stoichiometric RNA stain, proportional DNA stain, and proportional RNA stain.

10. The method of claim 9 wherein the step of marking the sample comprises staining with a stain selected from the group consisting of Feulgen stain, Romanowski stain, May-Grunwald-Giemsa stain, Methyl Green and thionin.

11. The method of claim 1 wherein the step of marking the sample comprises staining with an antibody marker.

12. The method of claim 1 wherein the step of marking the sample comprises staining with a nucleic acid sequence marker.

13. The method of claim 1 further comprising the step of selecting the at least one object of interest to include cancer diagnostics.

14. The method of claim 1 further comprising the step of selecting the at least one object of interest to include a preinvasive cancer cell.

15. The method of claim 14 wherein the preinvasive cancer cell is derived from an epithelial cancer.

16. The method of claim 15 wherein the epithelial cancer is selected from the group consisting of lung cancer, throat cancer, cervical cancer, ovarian cancer, breast cancer, prostate cancer, skin cancer and cancer of the gastrointestinal tract.

17. The method of claim 14 wherein the preinvasive cancer cell is derived from a neuroendocrine cancer.

18. The method of claim 17 wherein the neuroendocrine cancer is selected from the group consisting of lung and throat cancer, cervical cancer, breast cancer, and cancer of the gastrointestinal tract, lymphatic cancer and bone cancer.

19. The method of claim 1 further comprising the step of selecting the at least one object of interest to include an invasive cancer cell.

20. The method of claim 19 wherein the invasive cancer cell is derived from an epithelial cancer.

21. The method of claim 20 wherein the epithelial cancer is selected from the group consisting of lung cancer, throat cancer, cervical cancer, ovarian cancer, breast cancer, prostate cancer, skin cancer, cancer of the gastrointestinal tract, lymphatic cancer and bone cancer.

22. The method of claim 19 wherein the invasive cancer cell is derived from a neuroendocrine cancer.

23. The method of claim 22 wherein the neuroendocrine cancer is selected from the group consisting of lung cancer, throat cancer, cervical cancer, breast cancer, and cancer of the gastrointestinal tract, lymphatic cancer and bone cancer.

24. The method of claim 1 further comprising the step of using the at least one object of interest for screening a patient for cancer.

25. The method of claim 1 further comprising the step of using the at least one object of interest for determining whether a patient will develop invasive cancer.

26. The method of claim 1 further including the step of combining at least two projection images using methods for computerized image reconstruction to generate multi-dimensional images.

27. The method of claim 26 wherein the computerized image reconstruction methods include methods selected from the group consisting of fan beam projection geometries and cone beam projection geometries.

28. The method of claim 26 further comprising steps wherein the multi-dimensional images, are processed as follows:
   (a) compensating the multi-dimensional images for variations in background illumination;
   (b) analyzing the multi-dimensional images to detect at least one object of interest;
   (c) calculating a surface that bounds each object of interest;
   (d) calculating a set of multi-dimensional feature values for each object of interest; and
   (e) providing the set of multi-dimensional feature values to at least one classifier that identifies and characterizes cells of interest in the cell sample.

29. The method of claim 28 wherein the multi-dimensional feature values used to classify cells of interest in the sample are selected from the group consisting of 1D nuclear densitometric features (NDFs), 2D NDFs, 3D NDFs and 3D+ NDFs, 1D cytoplasmic densitometric features (CDFs), 2D CDFs, 3D CDFs and 3D+ CDFs, area, mean radius, volume, mean volume, optical density (OD) variance, OD skewness, OD range, OD average, OD maximum, density of light spots, low DNA volume, high DNA volume, low DNA amount, high DNA amount, high average distance, mid/high average distance, correlation, homogeneity, entropy, fractal dimension, DNA index, texture, punctateness, connected components and harmonics in spatial density frequency space.

30. The method of claim 28 wherein the multi-dimensional feature values include 1D, 2D, 3D and 3D+ features that are utilized by a classification program to characterize cells of interest with regard to type, maturation, disease status, relative abundance and presence of quantitative markers.

31. The method of claim 28 wherein the classifier detects and characterizes cells of interest including rare cells.

32. The method of claim 28 further including the step of diagnosing the cell sample based upon the characterization of cells.

33. The method of claim 1 wherein the at least one projection image comprises a shadowgram.

34. A method for identifying the at least one object of interest from a cell sample, comprising the steps of:
   (a) obtaining a cell sample and suspending the cells in solution;
   (b) if required, fixing the cells of the cell sample in solution;
   (c) marking the cells to generate optical densities within each cell of the sample;
   (d) illuminating the sample with at least one point source of light;
   (e) obtaining at least one projection image through the sample with a digital array detector;
   (f) compensating the at least one projection image for variations in background illumination;
   (g) analyzing the at least one projection image to detect at least one object of interest;
   (h) calculating a set of feature values having one-dimensional (1D) feature values and two-dimensional (2D) feature values for the at least one object of interest, wherein the set of feature values used to classify the at least one object of interest in the sample are selected from the group consisting of 1D nuclear densitometric features (NDFs), 2D NDFs, 1D cytoplasmic densitometric features (CDFs), 2D CDFs, area, mean radius, optical density (OD) variance, OD skewness, OD range, OD average, OD maximum, density of light spots, low DNA area, high DNA area, low DNA amount, high DNA amount, high average distance, mid/high average distance, correlation, homogeneity, entropy, fractal dimension, DNA index, texture, punctateness, connected components and harmonics in spatial density frequency space;
   (i) providing the set of feature values to at least one classifier; and
   (j) using the set of feature values and the at least one classifier for identifying the at least one object of interest from the cell sample.

* * * * *